US012152487B2

(12) United States Patent
Fripp et al.

(10) Patent No.: US 12,152,487 B2
(45) Date of Patent: Nov. 26, 2024

(54) FLUID IDENTIFICATION OUTSIDE OF WELLBORE TUBING

(71) Applicant: Halliburton Energy Services, Inc., Houston, TX (US)

(72) Inventors: Michael Linley Fripp, Singapore (SG); Luke William Holderman, London (GB); Xiang Wu, Singapore (SG); Yijing Fan, Singapore (SG)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 17/836,962

(22) Filed: Jun. 9, 2022

(65) Prior Publication Data
US 2023/0399943 A1    Dec. 14, 2023

(51) Int. Cl.
| | |
|---|---|
| *E21B 49/08* | (2006.01) |
| *E21B 47/113* | (2012.01) |
| *G01N 27/06* | (2006.01) |
| *G01N 27/22* | (2006.01) |
| *G01N 33/28* | (2006.01) |

(52) U.S. Cl.
CPC ............ *E21B 47/113* (2020.05); *E21B 49/08* (2013.01); *G01N 27/06* (2013.01); *G01N 27/221* (2013.01); *G01N 33/2823* (2013.01)

(58) Field of Classification Search
CPC ... E21B 49/08; E21B 47/113; G01N 33/2823; G01N 27/06; G01N 27/221
See application file for complete search history.

(56) References Cited

U.S. PATENT DOCUMENTS

| | | |
|---|---|---|
| 3,675,121 A | 7/1972 | Thompson |
| 4,009,434 A | 2/1977 | McKinlay et al. |
| 6,318,463 B1 | 11/2001 | Fehrmann et al. |
| (Continued) | | |

FOREIGN PATENT DOCUMENTS

| | | |
|---|---|---|
| WO | 2020257452 A1 | 12/2020 |
| WO | 2021025667 A1 | 2/2021 |

OTHER PUBLICATIONS

Wang, et al. "Novel Downhole Electromagnetic Flowmeter for Oil-Water Two-Phase Flow in High-Water-Cut Oil-Producing Wells", Sensors, 2016, 16, 1703, pp. 1-17.
(Continued)

*Primary Examiner* — D. Andrews
(74) *Attorney, Agent, or Firm* — Barnes & Thornburg LLP

(57) ABSTRACT

Apparatus and methods for measuring the oil to water ratio of a wellbore fluid. An example method includes flowing the wellbore fluid into a flow path of a fluid identification device disposed on the outside of a wellbore tubing and within a wellbore annulus. The fluid identification device comprises a shroud, the flow path disposed within the shroud that opens to the wellbore annulus and fluidically links the wellbore annulus to the wellbore tubing thereby allowing fluid flow through the flow path from the wellbore annulus to the wellbore tubing, and an alternating current electrical sensor disposed within the flow path. The method further includes measuring a property of the wellbore fluid with the alternating current electrical sensor when the wellbore fluid has flowed into the flow path and determining the oil to water ratio of the wellbore fluid that flowed through the flow path.

26 Claims, 10 Drawing Sheets

(56) References Cited

U.S. PATENT DOCUMENTS

| | | |
|---|---|---|
| 6,505,682 B2 * | 1/2003 | Brockman ............ E21B 43/128 |
| | | 166/250.15 |
| 6,755,086 B2 | 6/2004 | Salamitou et al. |
| 6,782,736 B1 | 8/2004 | Hammer |
| 7,276,916 B2 | 10/2007 | Hammer |
| 7,624,652 B2 | 12/2009 | Wee et al. |
| 8,610,895 B1 * | 12/2013 | Irani ........................ G01N 1/38 |
| | | 356/445 |
| 8,816,689 B2 | 8/2014 | Colombo et al. |
| 9,045,973 B2 | 6/2015 | Potyrailo et al. |
| 9,494,032 B2 | 11/2016 | Roberson et al. |
| 10,030,506 B2 | 7/2018 | Fanini et al. |
| 10,775,527 B2 | 9/2020 | Wilson et al. |
| 10,782,437 B2 | 9/2020 | Ewe et al. |
| 11,118,452 B1 * | 9/2021 | Yateem ................... G01F 25/10 |
| 2008/0127712 A1 | 6/2008 | Baker |
| 2009/0101329 A1 * | 4/2009 | Clem ...................... E21B 43/32 |
| | | 166/250.15 |
| 2016/0258290 A1 | 9/2016 | Murphree et al. |
| 2018/0283134 A1 * | 10/2018 | Ornelaz ................. E21B 43/14 |
| 2019/0242213 A1 | 8/2019 | Hunter |
| 2020/0240266 A1 | 7/2020 | Hunter et al. |

OTHER PUBLICATIONS

International Search Report and Written Opinion date mailed Feb. 27, 2023; International Application No. PCT/US2022/033615.

\* cited by examiner

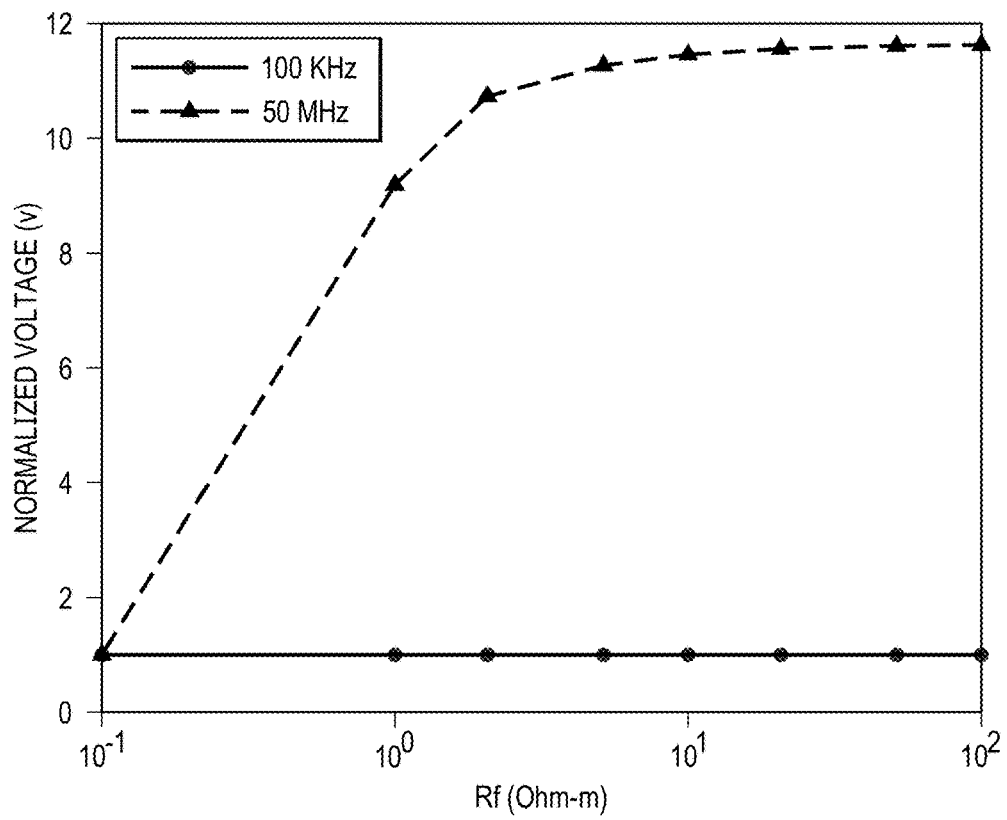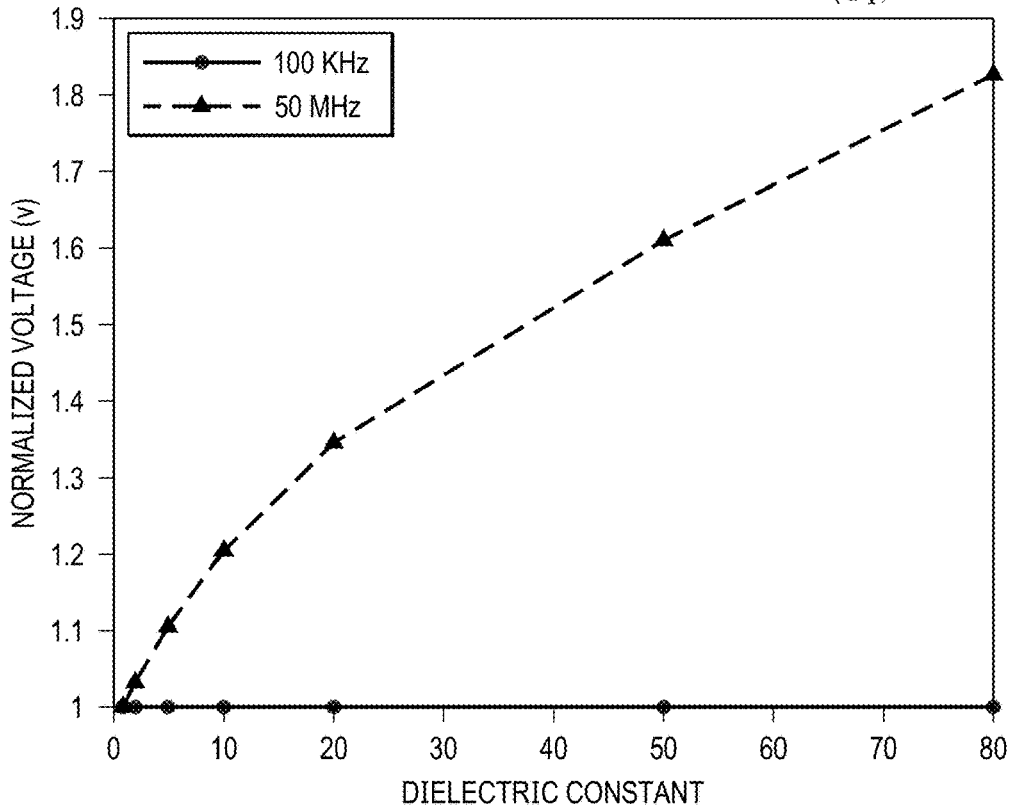
FIG. 8

FLUID IDENTIFICATION OUTSIDE OF WELLBORE TUBING

TECHNICAL FIELD

The present disclosure relates generally to production operations, and more particularly, to identifying the oil to water ratio of a wellbore fluid for a specific wellbore zone.

BACKGROUND

After a wellbore has been formed, natural resources such as hydrocarbons may be extracted from the wellbore. At various times during production, injection, and/or maintenance operations, it may be necessary to regulate fluid flow into or out of various portions of the wellbore or various portions of the downhole tools used in the wellbore. Additionally, for some operations it may simply be desirable to know what type of natural resources are being produced from a specific zone of the subterranean formation.

Provided are improvements to wellbore operations through the use of a sensor assembly configured to measure the dielectric permittivity and/or magnetic permeability of the incoming wellbore fluid as it flows into a flow path which is disposed outside of the production tubing and within the wellbore annulus. The measured dielectric permittivity and/or magnetic permeability may be used to determine the oil to water ratio of only the incoming wellbore fluid produced from the adjacent production zone.

BRIEF DESCRIPTION OF THE DRAWINGS

Illustrative examples of the present disclosure are described in detail below with reference to the attached drawing figures, which are incorporated by reference herein, and wherein:

FIG. 8 is a graph illustrating the charting of the received voltage versus the resistivity or the dielectric constant of a wellbore fluid in accordance with one or more examples described herein;

Figure 1:
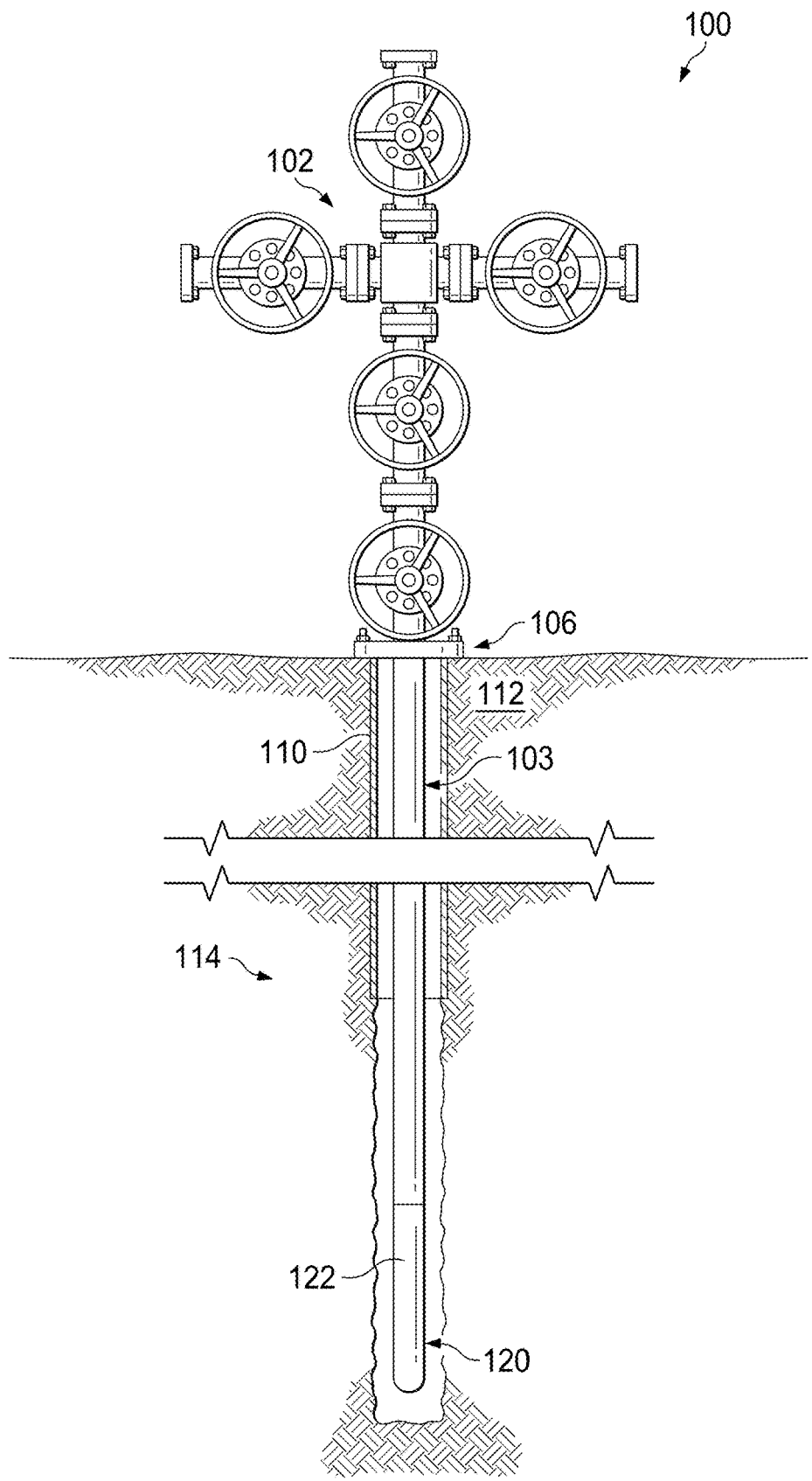
FIG. 1 is a cross-section illustrating a production operation in accordance with one or more examples described herein.

The illustrated figures are only exemplary and are not intended to assert or imply any limitation with regard to the environment, architecture, design, or process in which different examples may be implemented.

DETAILED DESCRIPTION

The present disclosure relates generally to production operations, and more particularly, to identifying the oil to water ratio of a wellbore fluid for a specific wellbore zone.

In the following detailed description of several illustrative examples, reference is made to the accompanying drawings that form a part hereof, and in which is shown by way of illustration, examples that may be practiced. These examples are described in sufficient detail to enable those skilled in the art to practice them, and it is to be understood that other examples may be utilized, and that logical structural, mechanical, electrical, and chemical changes may be made without departing from the spirit or scope of the disclosed examples. To avoid detail not necessary to enable those skilled in the art to practice the examples described herein, the description may omit certain information known to those skilled in the art. The following detailed description is, therefore, not to be taken in a limiting sense, and the scope of the illustrative examples is defined only by the appended claims.

Unless otherwise specified, any use of any form of the terms "connect," "engage," "couple," "attach," or any other term describing an interaction between elements is not meant to limit the interaction to direct interaction between the elements and may also include indirect interaction between the elements described. Further, any use of any form of the terms "connect," "engage," "couple," "attach," or any other term describing an interaction between elements includes items integrally formed together without the aid of extraneous fasteners or joining devices. In the following discussion and in the claims, the terms "including" and "comprising" are used in an open-ended fashion, and thus should be interpreted to mean "including, but not limited to." Unless otherwise indicated, as used throughout this document, "or" does not require mutual exclusivity.

The terms uphole and downhole may be used to refer to the location of various components relative to the bottom or end of a well. For example, a first component described as uphole from a second component may be further away from the end of the well than the second component. Similarly, a first component described as being downhole from a second component may be located closer to the end of the well than the second component.

The examples described herein relate generally to production operations, and more particularly, to identifying the oil to water ratio of a wellbore fluid for a specific wellbore zone. Advantageously, a fluid identification device is disposed outside of the wellbore tubing (e.g., a production tubing). The fluid identification device is also disposed within an annulus of the wellbore. The fluid identification device may be disposed proximate to a zone of the subterranean formation in which it is desirable to determine the oil to water ratio of the wellbore fluid produced from the production zone. As a further advantage, the fluid identification device comprises a sensor assembly disposed within a flow path of the fluid identification device. The flow path opens to but is distinctly separate from the wellbore annulus. Although the fluid identification device is disposed within the wellbore annulus, the sensors of the fluid identification device are not disposed in the wellbore annulus or the wellbore tubing. This sensor arrangement allows the oil to water ratio to be determined for only the fluid flowing into the flow path. The sensor assembly does not sense the fluid already in the wellbore tubing. The sensor assembly does not sense the fluid in the proximate production zone of the subterranean formation. Fluid within the proximate production zone may remain in the zone and not actually flow into the wellbore to be produced. The sensor assembly will only sense the fluid exiting the proximate production zone of the subterranean formation and flowing from the wellbore annulus into the flow path of the fluid identification device. As such, the sensor assembly allows for the determination of the oil to water ratio of only the wellbore fluid produced from the targeted proximate production zone of the subterranean formation and not fluid merely residing in said zone or wellbore annulus. As a further advantage, the sensors may measure the dielectric permittivity and/or the magnetic permeability of the wellbore fluid in order to determine the oil to water ratio of the fluid. Another advantage is that the sensors may be encapsulated to reduce corrosion or other such degradation of the sensor components. The sensors may be arranged in a variety of configurations. A flow conditioner may be added upstream of the sensors. The flow conditioner may adjust the flow to a known state for increasing measurement accuracy. In some examples, the fluid identification device may comprise a flow regulator such as inflow control valve to control the fluid flow into the wellbore tubing. Advantageously, the precise adjustment of the fluid flow may be determined by the determined oil to water ratio.

FIG. 1 is a cross-section of a well system, generally 100. Well system 100 may include well surface or well site 106. Various types of equipment such as production fluid pumps, production tubing, or production equipment may be located at well surface or well site 106. For example, well site 106 may include surface Christmas tree 102 that may have various characteristics and features associated with a land operation. However, downhole tools incorporating teachings of the present disclosure may be satisfactorily used with equipment located on offshore platforms, ships, semi-submersibles, barges, etc. (not expressly shown).

Well system 100 may also include wellbore tubing 103, which may be used to produce hydrocarbons such as oil and gas and other natural resources such as water from formation 112 via wellbore 114. Wellbore tubing 103 may also be used to inject hydrocarbons such as oil and gas and other natural resources into formation 112 via wellbore 114. As shown in FIG. 1, wellbore 114 is substantially vertical (e.g., substantially perpendicular to the surface). Although not illustrated in FIG. 1, portions of wellbore 114 may be substantially horizontal (e.g., substantially parallel to the surface), or at an angle between vertical and horizontal. Casing string 110 may be placed in wellbore 114 and held in place by cement, which may be injected between casing string 110 and the sidewalls of wellbore 114. Casing string 110 may provide radial support to wellbore 114 and may seal against unwanted communication of fluids between wellbore 114 and surrounding formation 112. Casing string 110 may extend from well surface 106 to a selected downhole location within wellbore 114. Portions of wellbore 114 that do not include casing string 110 may be referred to as open hole.

Well system 100 may also include downhole assembly 120 coupled to wellbore tubing 103. Downhole assembly 120 may be used to perform operations relating to completion of wellbore 114, production of hydrocarbons and other natural resources from formation 112 via wellbore 114, injection of hydrocarbons and other natural resources into formation 112 via wellbore 114, and/or maintenance of wellbore 114. Downhole assembly 120 may be located at the end of wellbore 114 or at a point uphole from the end of wellbore 114. Downhole assembly 120 may be formed from a wide variety of components configured to perform these operations. For example, component 122 may include, but are not limited to, fluid identification devices, screens, slotted tubing, packers, valves, sensors, actuators, etc. The number and types of components 122 included in downhole assembly 120 may depend on the type of wellbore 114, the operations being performed in the wellbore 114, and anticipated wellbore conditions. In the present example component 122 is a fluid identification device.

Fluids may be extracted from or injected into wellbore 114 via downhole assembly 120 and wellbore tubing 103. For example, production fluids, including hydrocarbons, water, sediment, and other materials or substances found in formation 112 may flow from formation 112 into wellbore 114 through the sidewalls of open hole portions of wellbore 114. The production fluids may circulate in wellbore 114 before being extracted from wellbore 114 via downhole assembly 120 and wellbore tubing 103. Additionally, injection fluids, including hydrocarbons, water, and other materials or substances, may be injected into wellbore 114 and formation 112 via wellbore tubing 103 and downhole assembly 120. Fluid identification device 122 may monitor and optionally, control the fluids flowing between wellbore 114 and downhole assembly 120. Downhole assembly 120 may be in communication with a signaling device, such as a telemetry system, that is displaced from downhole assembly 120 and that signals downhole assembly 120 or the fluid identification device 122 to increase or decrease the flow resistance provided by the flow control device. For example, the signaling device may be located at well site 106, within wellbore 114 at a location different from the location of downhole assembly 120, or within a lateral wellbore.

Figure 2A:
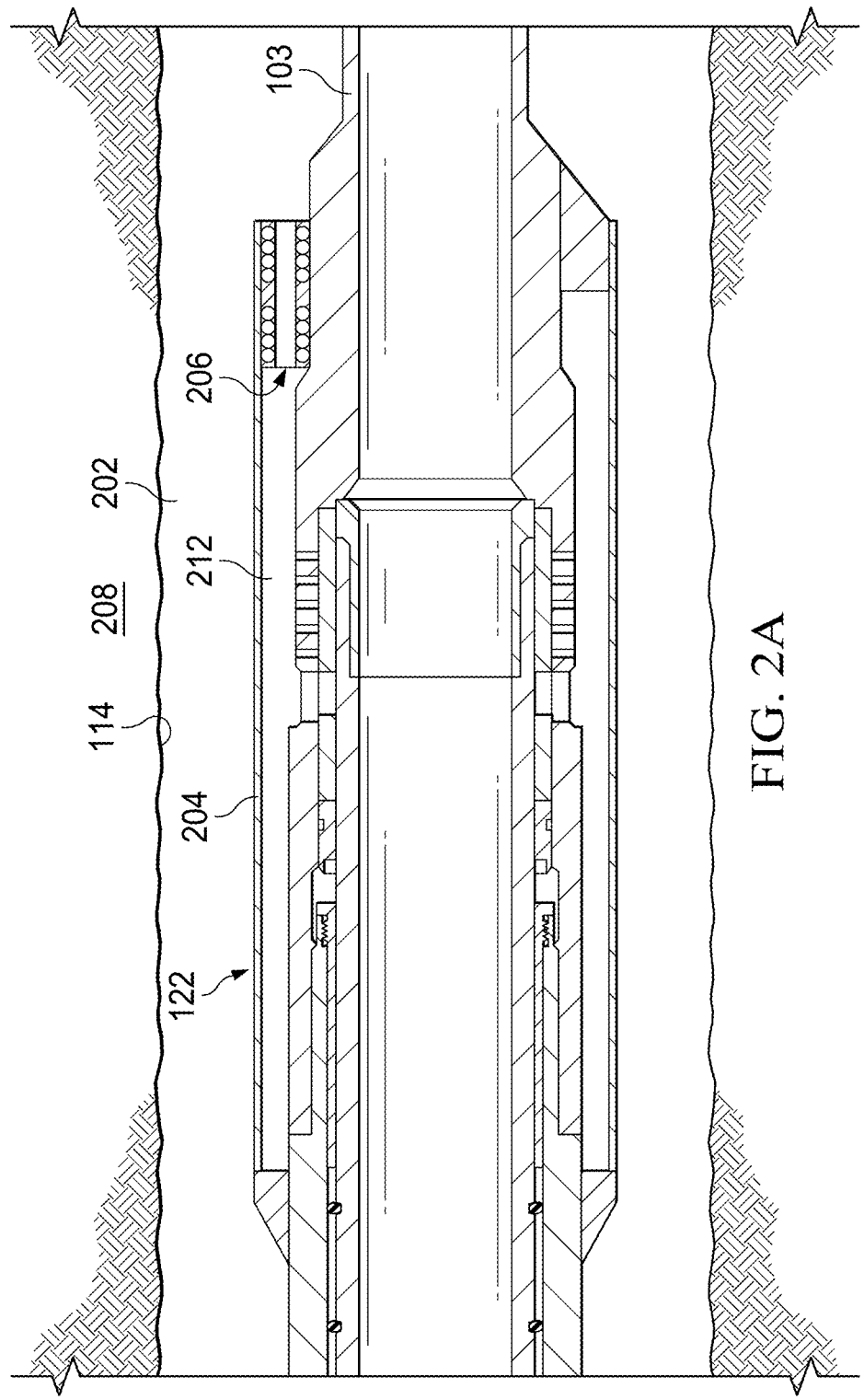
FIG. 2A is a cross-section illustrating a fluid identification device in accordance with one or more examples described herein.

FIG. 2A is a cross-sectional view of a fluid identification device 122, which may be a subcomponent of a downhole assembly 120 discussed in FIG. 1 above. Production fluids circulating in wellbore 114 may flow through fluid identification device 122 into wellbore tubing 103. Fluid identification device 122 is coupled to the exterior of wellbore tubing 103. Fluid identification device 122 may be coupled to wellbore tubing 103 by a threaded joint or any suitable connection. The coupling of fluid identification device 122 to wellbore tubing 103 may provide a fluid and pressure tight seal.

Fluid identification device 122 comprises a shroud 204. The shroud 204 may be coupled to and disposed around the circumference of wellbore tubing 103 such that a flow path 212 is formed between the inner surfaces of shroud 204 and the outer surface of wellbore tubing 103. The flow path 212 is thus outside of the wellbore tubing 103 while also restricting fluid flow inward from the wellbore annulus 202 of wellbore 114. The flow path 212 only allows inward fluid flow from the proximate zone 208 of the subterranean formation. Fluid remaining in the proximate zone 208 does not flow through the flow path 212 if it does not exit the proximate zone 208. Fluid flowing through the wellbore tubing 103 does not enter the flow path 212.

Within the flow path 212 is a sensor assembly 206. Fluid flowing from the proximate zone 208 of the subterranean formation may be sensed by the sensor assembly 206 as it flows through flow path 212. Although the fluid identification device 122 is disposed within the wellbore annulus 202, the sensor assembly 206 of the fluid identification device 122 is not disposed in the wellbore annulus 202 or the wellbore tubing 103. This sensor assembly 206 allows the oil to water ratio to be determined for only the wellbore fluid flowing into the flow path 212. The sensor assembly 206 does not sense the fluid already in the wellbore tubing 103. The sensor assembly 206 does not sense the fluid remaining in the proximate zone 208 of the subterranean formation that does not flow into the wellbore annulus 202. The sensor assembly 206 will only sense the wellbore fluid exiting the proximate zone 208 of the subterranean formation and flowing from the wellbore annulus 202 into the flow path 212 of the fluid identification device 122. As such, the sensor assembly 206 allows for the determination of the oil to water ratio of only the wellbore fluid produced from the targeted proximate zone 208 of the subterranean formation and not merely residing in said proximate zone 208.

Figure 2B:
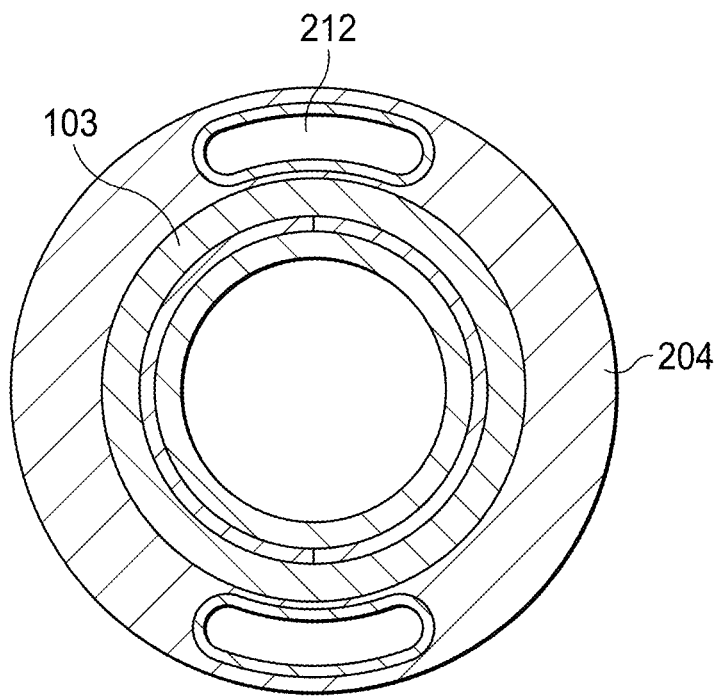
FIG. 2B is a cross-section illustrating another view of a fluid identification device in accordance with one or more examples described herein.

FIG. 2B is a cross-section of the fluid identification device 122 of FIG. 2A illustrating another view of the wellbore tubing 103, the shroud 204, and the flow path 212. As illustrated the flow path 212 is a distinct and separate flow path from the wellbore annulus 202 and the interior of wellbore tubing 103.

Figure 2C:
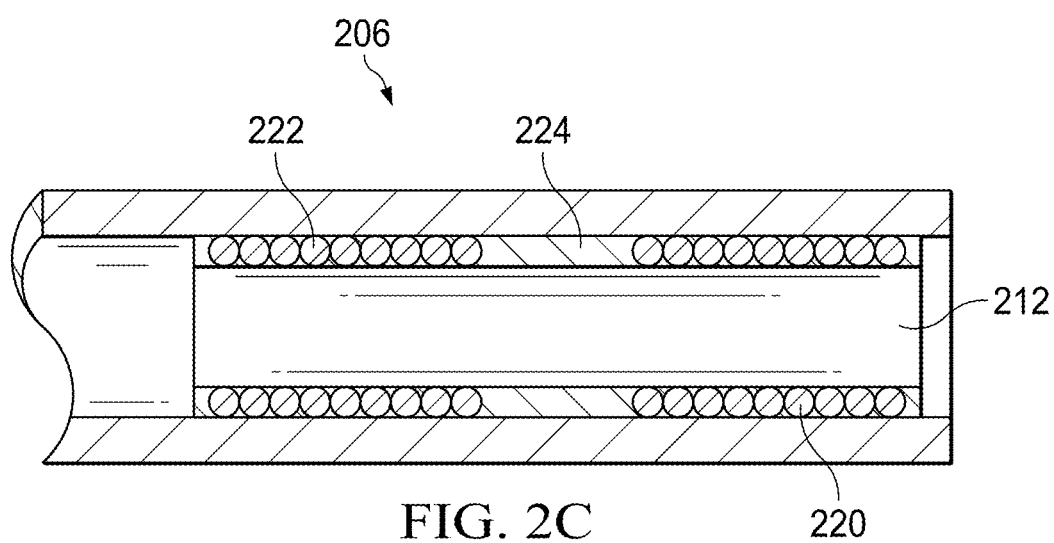
FIG. 2C is a cross-section illustrating another view of a fluid identification device in accordance with one or more examples described herein.

FIG. 2C is an enlarged view of the sensor assembly 206 of the fluid identification device 122 of FIG. 2A. Sensor assembly 206 comprises a transmitting portion 220 (e.g., a transmitting coil) and receiving portion 222 (e.g., a receiving coil) which are positioned in an encapsulation layer 224 which prevents contact of the transmitting portion 220 and receiving portion 222 with the incoming wellbore fluid. The transmitting portion 220 and receiving portion 222 form an AC electrical sensor. The AC electrical sensor transmits an AC electromagnetic signal via the transmitting portion 220 and then receives the AC electromagnetic signal via the receiving portion 222. The AC electromagnetic signal generated by the transmitting portion 220 is distorted by the fluid within the flow path 212. The signal is then electrically detected by the receiving portion 222. A combination of AC electromagnetic signals may be used to more accurately identify the constituents of the wellbore fluid in some optional examples.

As an example, the type of AC electrical sensor is a capacitive sensor measuring the relative dielectric permittivity of the wellbore fluid. The relative dielectric permittivity of water is about 80 and the relative dielectric permittivity of oil is about 4. The exact values will vary with the type of oil, with temperature, and with the salts in the water. The exact values also vary with frequency, which may be used to help identify the different fluids. The relative phase between the induced current and the induced voltage can be used to identify the fluids. The algorithm for estimating the fluid fractions can include the transmitted voltage amplitude, the transmitted current amplitude, the phase between the transmitted voltage and current, the received voltage amplitude (when 2 sensors of the same type are used), the relative amplitude and phase of the transmitted and received voltage, the temperature, the properties of the pure fluid, pressure, and the flow speed. Measuring temperature may be important in some examples for updating the dielectric behavior because in many examples the dielectric of water changes much more significantly than for hydrocarbons with respect to temperature. In one example, a sinusoidal 10 kHz voltage signal is generated between two electrodes that form a capacitive sensor. The electrodes are circumferential around the flow path and the two electrodes are axially spaced approximately 1 cm apart. The ratio of the applied voltage and the measured current is proportional to the capacitance of the fluid between the electrodes. The phase between the applied voltage and current indicates the electrical resistance of the fluid between the electrodes. The water cut and liquid cut can be determined with the knowledge of the flow regime, the fluid capacitance, and the fluid resistance.

In another example, the type of AC electrical sensor is an inductive sensor measuring the relative magnetic permeability as well as the resistivity of the fluid. Some of the component fluids in the wellbore fluid may have similar magnetic permeabilities. However, brines have much lower resistivity than hydrocarbons. The AC magnetic field generated by the transmitting portion 220 causes an ionic current to flow that varies with the conductivity of the fluid. The transmitting portion 220 induces eddy currents in the brine distorting the magnetic signal. The receiving portion 222 detects whether a hydrocarbon or water is the continuous phase of the wellbore fluid as it flows through the flow path 212. As a result, the inductive sensor formed by the transmitting portion 220 and receiving portion 222 are creating a measurement of the conductivity of the wellbore fluid as well as a measure of the dielectric constant of the wellbore fluid. In one example, an electromagnetic signal is generated from a transmitting coil 222 by applying an oscillating voltage at 100 kHz and 50 MHz. The oscillating voltage is a square wave and alternates every 1 millisecond between providing the 100 kHz signals and 50 MHz signals with a 50% duty cycle for each frequency. An algorithm compares the ratio of the received and transmitted voltage amplitude at both frequencies. The voltage ratio indicates the dielectric permittivity of the fluid. The algorithm compares the relative phase of the transmitted current and voltage and the relative phase of the received current and voltage. The relative phase indicates the dielectric loss which is proportional to electrical conductivity. Using two frequencies allows for increased resolution because the real part and the imaginary part of dielectric measurements change with frequency. For many salt types and for many salt concentrations, the magnitudes decrease with increasing frequency, but this will vary with the water fraction in a well-mixed fluid. In another example, the lower frequency signal is used as a measure of the fluid resistivity because the conductivity term tends to dominate the dielectric term of the wave number in Maxwell's equation for most salt types and salt concentrations in a brine. The higher frequency signal is used as a measure of the dielectric properties of the fluid because the dielectric term of the wave number tends to dominate at higher frequencies.

It is to be understood that multiple sensors may be employed in some examples. Multiple capacitive sensors may be used in some sensor assemblies 206. In other examples, multiple inductive sensors may be used. In additional examples, both capacitive and inductive sensors may be used.

In some examples the sensor assembly 206 utilizes electrochemical impedance spectroscopy to analyze the dielectric constant of the fluid across a wide frequency range, often from Hz to GHz. The impedance spectrum contains information about the ohmic resistance of the fluid, the electron transfer resistance, and the Warburg diffusion impedance.

In some examples, sweeping across a wide range of frequencies may take too long and the fluid properties may change during the frequency sweep. In some cases, the AC electrical signal has a plurality of discrete frequencies which may approximate the frequency sweep but in a shorter time. These signals may be used sequentially or simultaneously. In another case, the AC electrical signal comprises broadcasting the entire frequency sweep simultaneously in the form of a frequency-weighted band-limited white noise. Discrete frequencies use simpler calculations while the white noise signal is likely to need a numerically intensive transfer function calculation.

Optionally, the sensor assembly 206 is encapsulated with an encapsulation layer 224. Encapsulation may prevent a wellbore fluid, such as a brine, from depositing scale on the sensor assembly 206 and may also minimize the electrochemical corrosion of the sensor assembly 206. In these examples, the transmitting portion 220 and the receiving portion 222 do not contact the fluid, and the sensor assembly 206 functions as an electrodeless fluid identification sensor. The encapsulation layer 224 may comprise a plastic or any type of polymeric material. The encapsulation layer should be thin enough to not short out the sensor assembly 206, yet also prevent the sensor assembly 206 from directly contacting the wellbore fluid.

Figure 3:
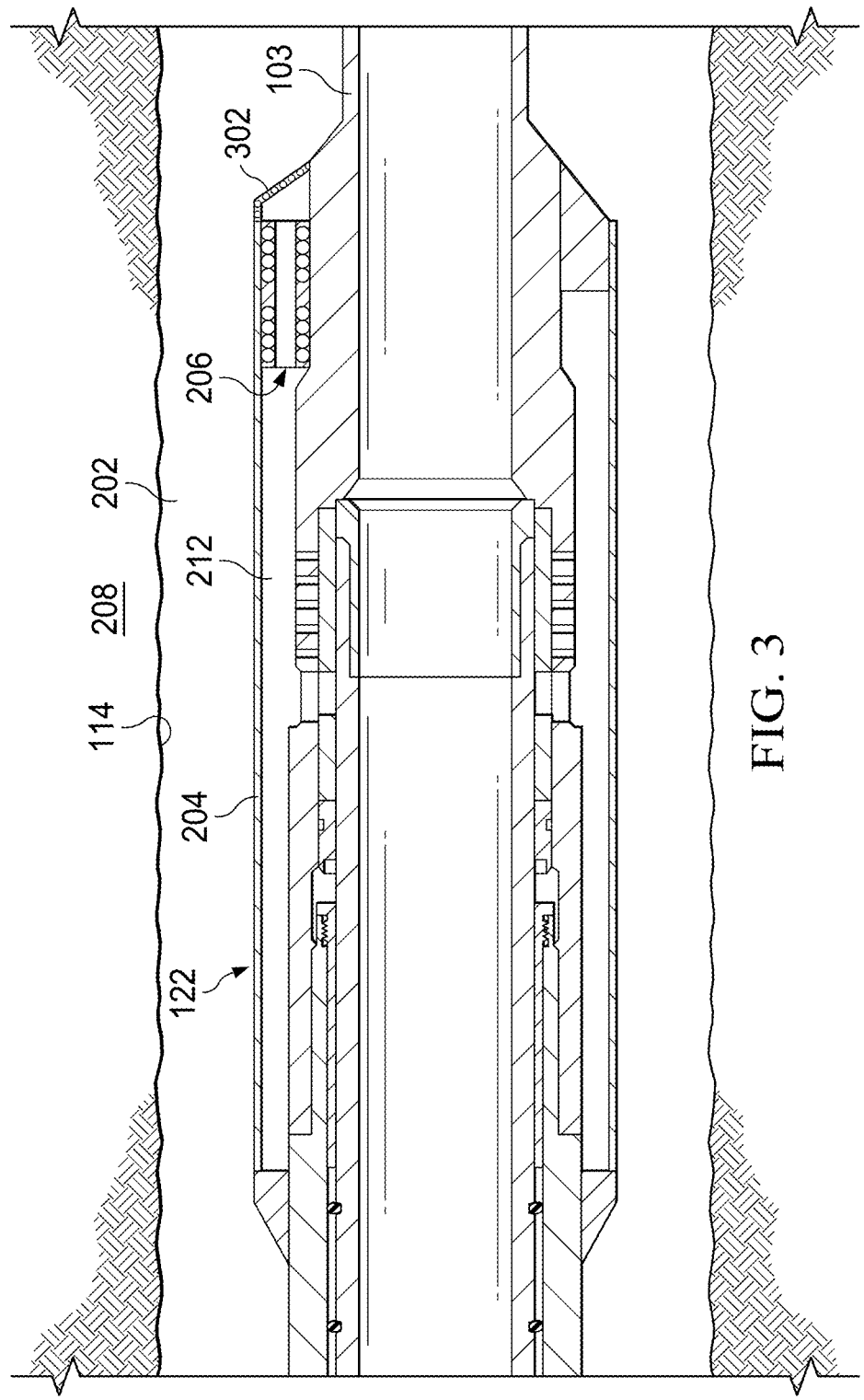
FIG. 3 is a cross-section illustrating the fluid identification device of FIG. 2A-2C further comprising a screen in accordance with one or more examples described herein.

FIG. 3 is a cross-sectional view of the fluid identification device 122 of FIGS. 2A-2C modified to include screen 302. Screen 302 may be coupled to and disposed downstream of sensor assembly 206. Both screen 202 and shroud 204 may be coupled to and disposed around the circumference of wellbore tubing 302 such that flow path 212 is formed between the inner surfaces of screen 302 and shroud 204 and the outer surface of wellbore tubing 103. Screen 302 may be configured to filter sediment from the wellbore fluid as it flows through screen 302. Examples of screen 302 may include, but are not limited to, a sand screen, a gravel filter, a mesh, or slotted tubing.

Figure 4:
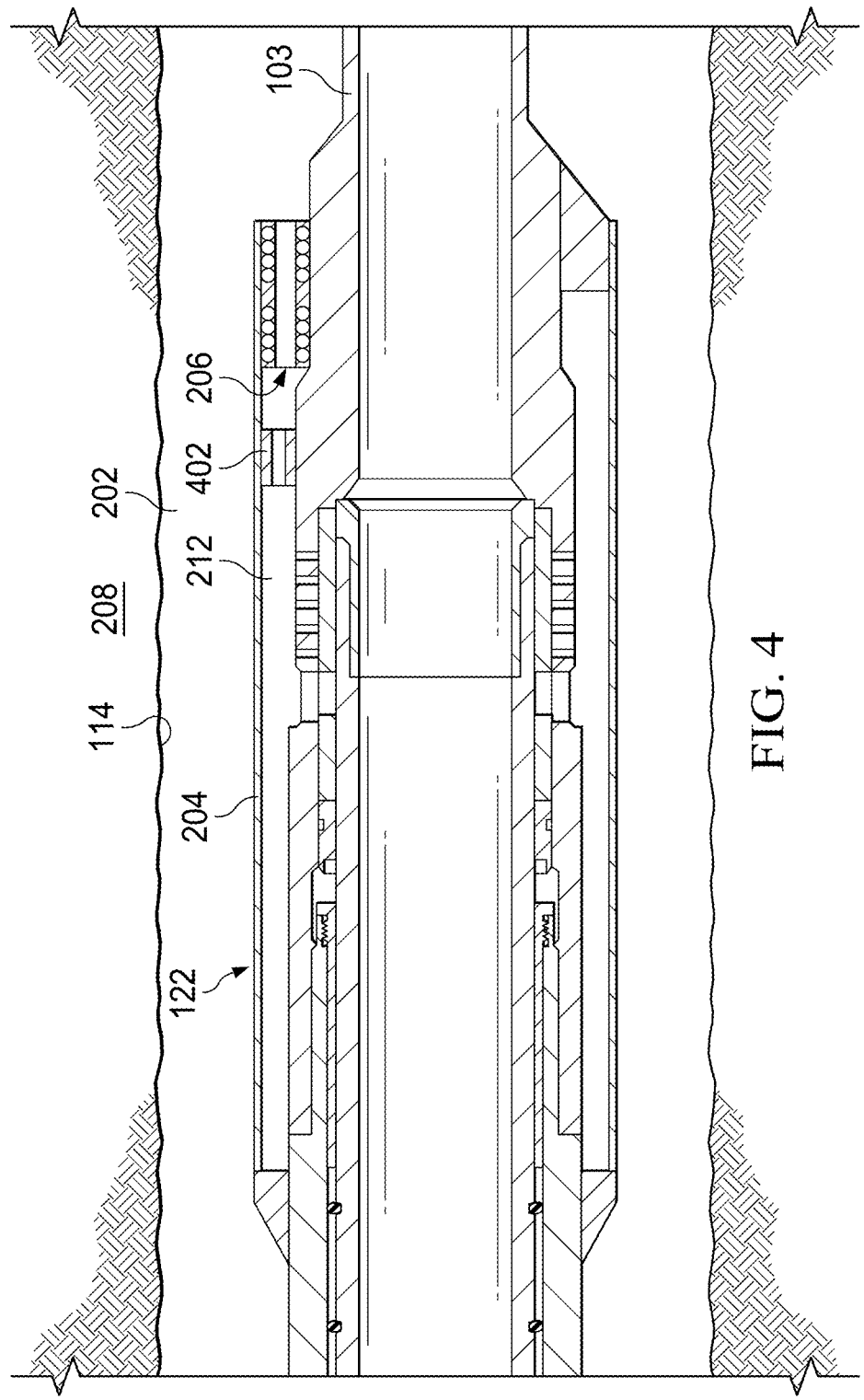
FIG. 4 is a cross-section illustrating the fluid identification device of FIG. 2A-2C further comprising a flow regulator in accordance with one or more examples described herein.

FIG. 4 is a cross-sectional view of the fluid identification device 122 of FIGS. 2A-2C modified to include flow regulator 402. Flow regulator 402 is disposed within flow path 212 between the inner surface of the shroud 204 and the exterior surface of the wellbore tubing 103. Flow regulator 402 is disposed downstream of sensor assembly 206. Flow regulator 402 may engage with shroud 204 and wellbore tubing 103 to prevent a wellbore fluid circulating within flow path 212 from flowing into wellbore tubing 103. For example, flow regulator 402 may form a fluid tight seal with the inner surface of shroud 204 and the outer surface of wellbore tubing 103. Additionally, the flow regulator 402 may regulate the rate of fluid flow through fluid identification device 122 by adjusting the flow resistance provided by flow regulator 402. Flow regulator 402 may be in communication with a signaling device, such as telemetry system, that is displaced from flow regulator 402 and signals flow regulator 402 to increase or decrease the flow resistance provided by flow regulator 402. The signaling device may be located at a well site surface or within wellbore 114 at a location different from the location of the flow regulator 402 or within a lateral wellbore. In some examples, the sensor assembly 206 may directly control the flow regulator 402 either through commands from the wellsite surface based on the data obtained from the sensor assembly 206, or the flow resistance of the flow regulator 402 may be adjusted automatically as programmed based on data obtained from the sensor assembly 206. An increase in the flow resistance provided by flow regulator 402 may result in a corresponding decrease in the rate of fluid flow through wellbore tubing 103, while a decrease in the flow resistance provided by flow regulator 402 may result in a corresponding increase in the rate of fluid flow through wellbore tubing 103. Although a single flow regulator 402 is illustrated, in some examples multiple flow regulators 402 may be utilized to regulate fluid flow from wellbore 114 into wellbore tubing 103. Flow regulator 402 may comprise a fixed valve such as a nozzle or an autonomous inflow control device or it may comprise an adjustable valve such as a sleeve, an inflow control valve, a ball valve, a smart well node, or other such mechanism for adjusting fluid flow. In one example, a smart well node may automatically adjust the flow restriction based on the measured flow composition. In another example, the smart well node may be a wireless smart well node and contain a generator that converts flow energy into electrical energy such as a turbine power generator.

Figure 5:
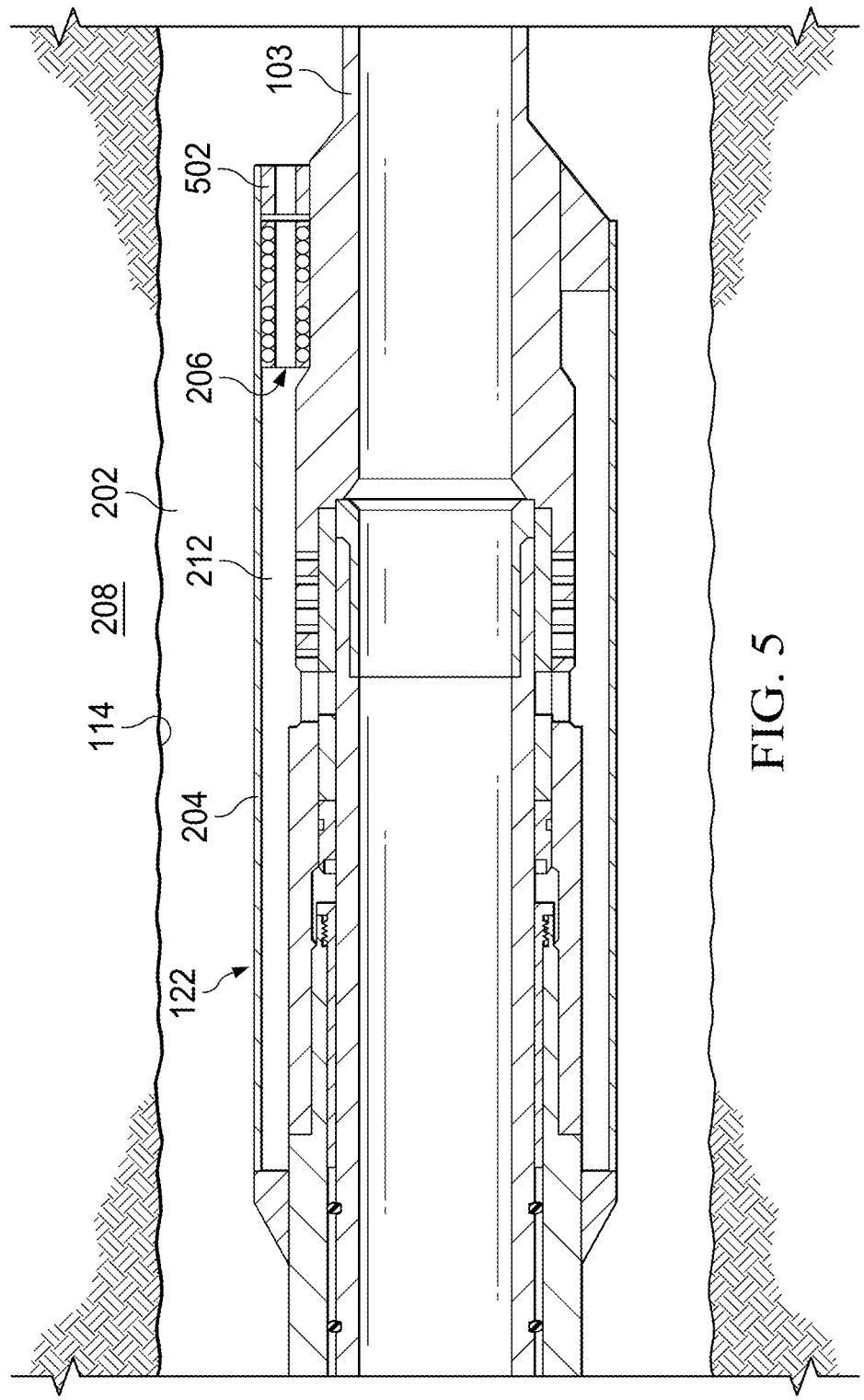
FIG. 5 is a cross-section illustrating the fluid identification device of FIG. 2A-2C further comprising a flow conditioner in accordance with one or more examples described herein.

FIG. 5 is a cross-sectional view of the fluid identification device 122 of FIGS. 2A-2C modified to include flow conditioner 502. Flow conditioner 502 is disposed within the flow path 212 between the inner surface of the shroud 204 and the exterior surface of the wellbore tubing 103. Flow conditioner 502 is disposed upstream of sensor assembly 206. Flow conditioner 502 may aid the sensor assembly 206 in obtaining the desired measurements. For example, the flow conditioner 502 may comprise a static mixer to ensure that the incoming wellbore fluid is flowing at regulated velocity. This also ensures that the flow conditions are turbulent. In another example, turbulent flow conditions may be achieved with a nozzle or alternative flow restrictor. In some examples, the flow conditioner 502 comprises a flow straightener that would minimize swirl, turbulence intensity, flow non-symmetry, dynamic pulsations, etc. while also producing a more fully developed flow behavior.

It is to be understood that although screen 302 of FIG. 3, flow regulator 402 of FIG. 4, and flow conditioner 502 of FIG. 5 are illustrated in distinct illustrations, these optional components may be used in combination with one another. For example, the fluid identification device 122 may comprise a screen 302, flow regulator 402, and flow conditioner 502. As another example, the fluid identification device 122 may comprise a screen 302 and a flow regulator 402. As a further example, the fluid identification device 122 may comprise a screen 302 and a flow conditioner 502. Any combination of these components may be used in fluid identification device 122.

Figure 6:
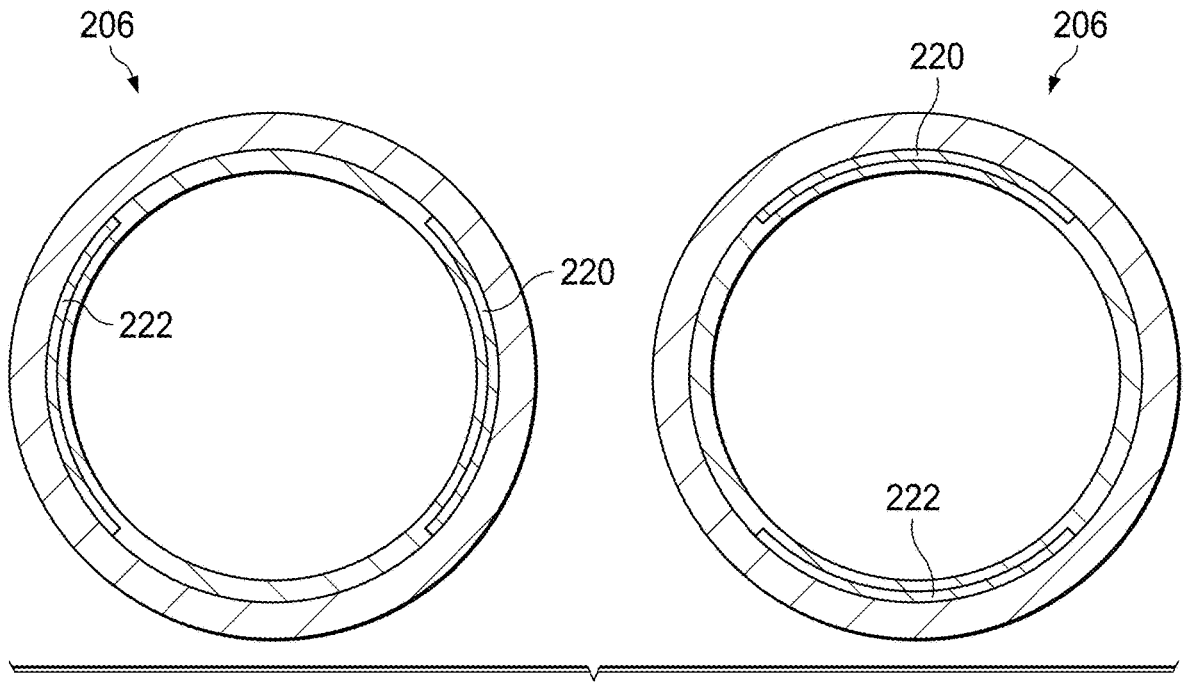
FIG. 6 is a cross-section illustrating potential sensor assemblies in accordance with one or more examples described herein.

FIG. 6 is a cross-section illustrating an alternative arrangement for the transmitting portion 220 and receiving portion 222 when the sensor assembly 206 is a capacitive sensor. In the illustrated example, a pair of transmitting portions 220 and receiving portions 222 are shown as orthogonal to one another with one of the pair vertically arranged relative to the fluid flow and the other horizontally arranged relative to the fluid flow. This arrangement of the capacitive sensors may help differentiate stratification within the fluid.

Figure 7:
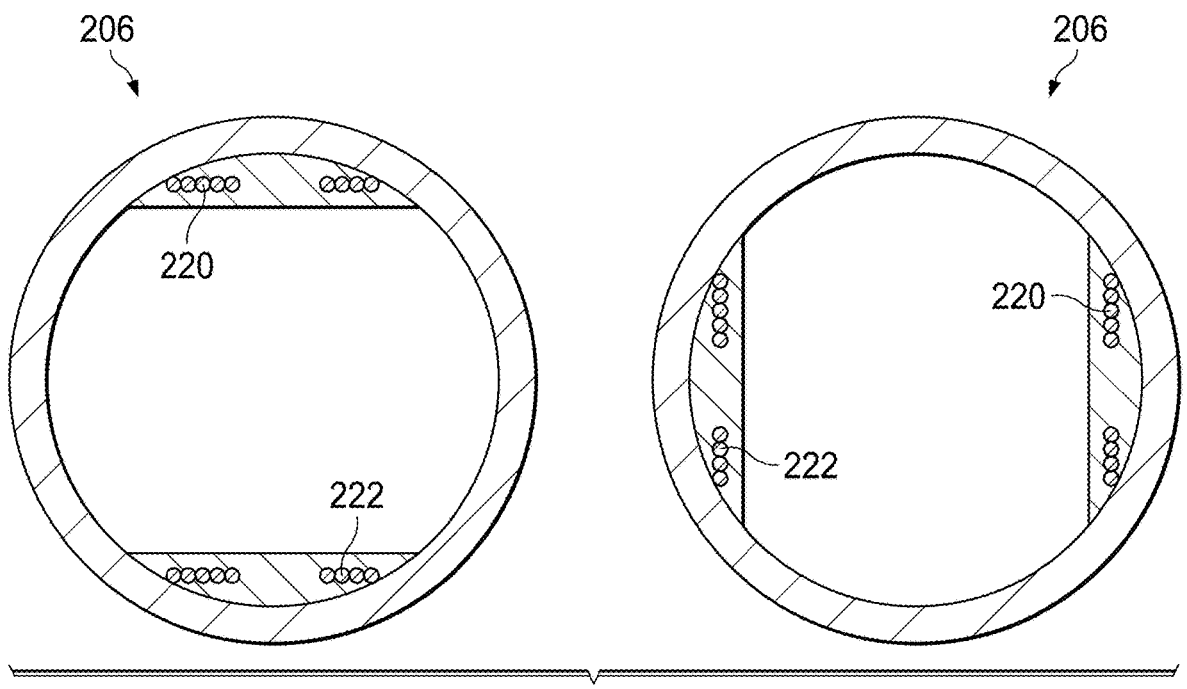
FIG. 7 is a cross-section illustrating additional potential sensor assemblies in accordance with one or more examples described herein.

FIG. 7 is a cross-section illustrating an alternative arrangement for the transmitting portion 220 and receiving portion 222 when the sensor assembly 206 is an inductive sensor. In the illustrated example, a pair of transmitting portions 220 and receiving portions 222 are shown as orthogonal to one another with one of the pair vertically arranged relative to the fluid flow and the other horizontally arranged relative to the fluid flow. For example, one transmitting portion 220 may be axial to the fluid flow while another transmitting portion 220 is perpendicular to the fluid flow. The sensor assembly 206 may also be reconfigured to comprise less than or more than the illustrated number of transmitting portions 220 and/or receiving portions 222. For example, one transmitting portion 220 may be sufficient to transit voltage that may be measured by two receiving portions 222. Alternatively, two transmitting portions 220 could transmit voltage to a single receiving portion 222.

Other alternative arrangements for the sensor assembly 206 include arranging the transmitting portion 220 and receiving portion 222 orthogonally, in a series, in a spiral around the flow path 212. Multiple arrangements of multiple sensor assemblies 206 may be used within the same fluid identification device 122.

FIG. 8 illustrates the response from an inductive sensor comprising a transmitting portion (i.e., a transmitting coil) and a receiving portion (i.e., receiving coil) located proximate each other. The left graph illustrates the received voltage versus resistivity. The right graph illustrates the received voltage versus the dielectric constant. As such, the graphs illustrate how the sensor assembly allows for the plotting of the voltage received at the receiving coil as a function of the properties of the wellbore fluid. Significant changes are seen as a function of the resistance of the fluid as well as of the relative dielectric permittivity of the fluid. Larger signals are measured at 50 MHz than at 100 kHz.

Figure 9:
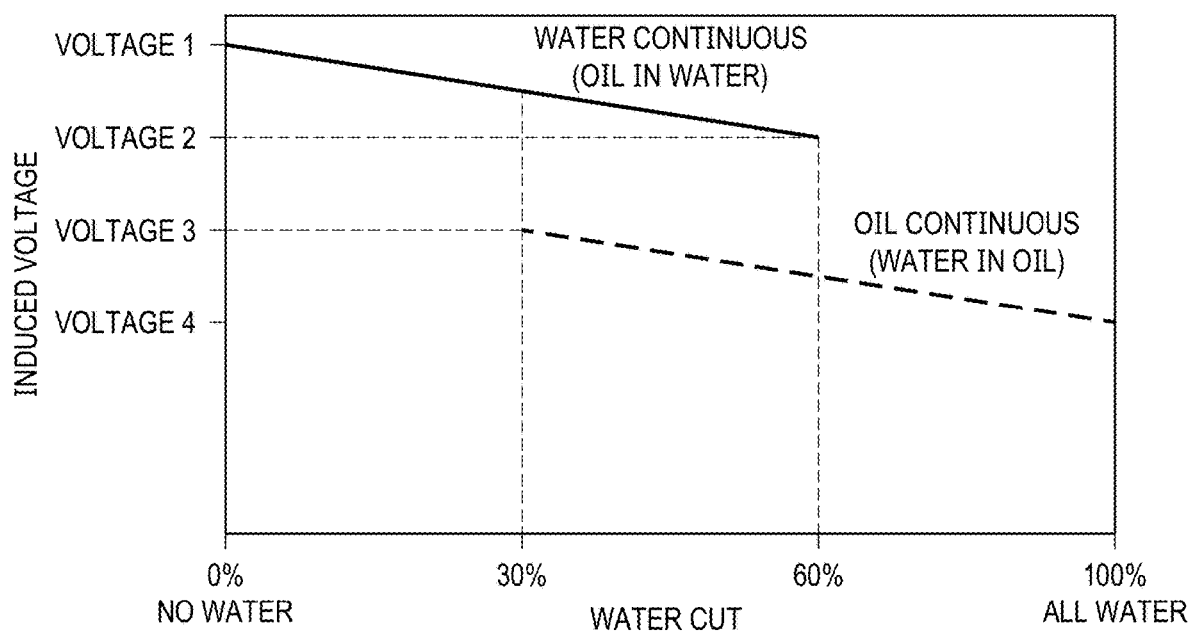
FIG. 9 is a graph illustrating how the induced voltage may be used to determine the oil to water ratio of a wellbore fluid in accordance with one or more examples described herein.

FIG. 9 illustrates how the sensor assembly (i.e., the AC electrical sensor) may be used to help distinguish whether the mixed water-hydrocarbon flow has a continuous phase of water or a continuous phase of hydrocarbon. If the flow was a continuous phase of water, then there would be droplets of oil in the water, and the entire wellbore fluid would be more conductive. There may be an overlap of values depending on the nature of the continuous phase. The induced voltage may be used to identify the continuous phase. As shown in FIG. 9, there is an overlap between roughly 30% and roughly 60% water cut. However, the bistability of the induced voltage may be used to determine the water ratio. If the induced voltage is between V1 and V2, then water is the continuous phase. If the induced voltage is between V3 and V4, then oil is the continuous phase.

Figure 10:
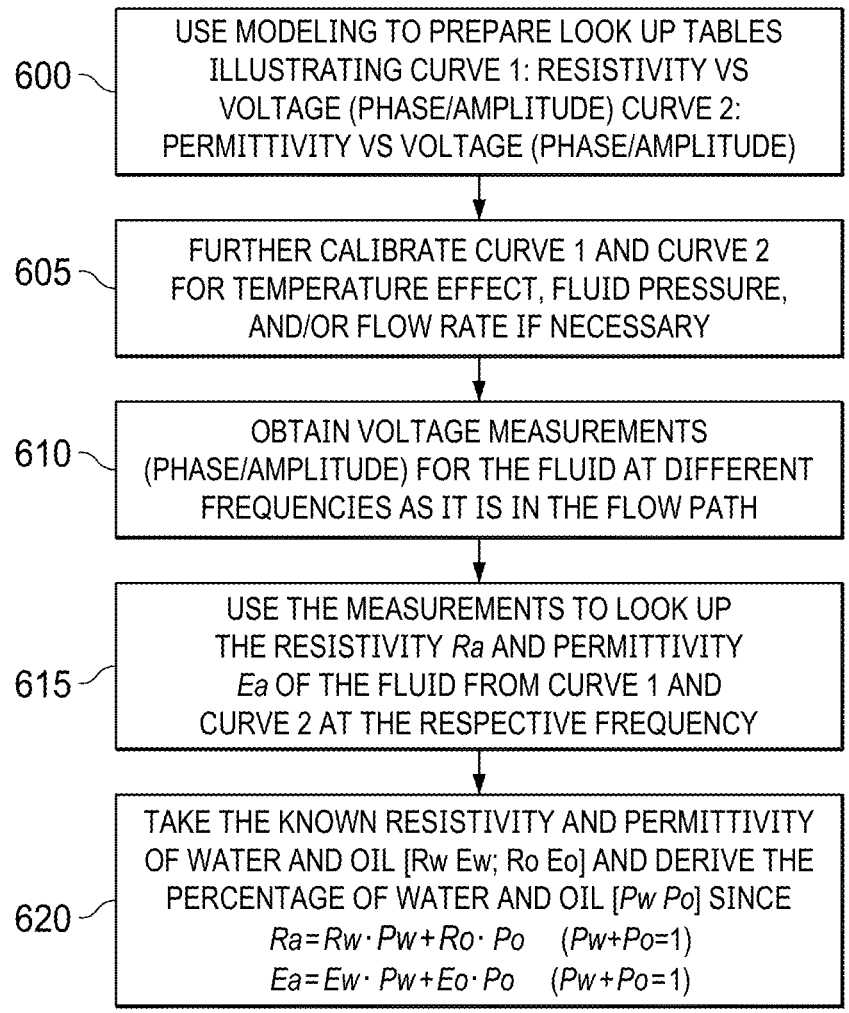
FIG. 10 is a flowchart illustrating an example method for determining the oil to water ratio of a wellbore fluid.

FIG. 10 is a flowchart illustrating one possible method for obtaining the oil to water ratio of a wellbore fluid. In box 600, look up tables may be prepared using experimental data or previously obtained wellbore data of the phase/amplitude of wellbore fluids. Two curves may be prepared that illustrate resistivity vs voltage and/or permittivity vs voltage. Examples of these curves are illustrated in FIG. 8. Box 605 details the optional calibration of the curves to account for the temperature, flow rate, and fluid pressure. The calibration may be done using experimental data or previously obtained wellbore data. At box 610, the sensor assembly obtains the phase/amplitude measurements for the wellbore fluid while it is flowing within the flow path of the fluid identification device. At box 615, the curves may be used to obtain the resistivity and permittivity values from the obtained phase/amplitude measurements. At box 620, the resistivity and permittivity values are used to obtain the oil to water ratio of the wellbore fluid that flowed through the flow path.

It is to be understood that the fluid identification device 122 and its components as depicted in FIGS. 1-7 are only one possible configuration of the fluid identification device 122. The individual pieces of the fluid identification device 122 may be rearranged as would be readily apparent to one of ordinary skill in the art. As such, it is to be recognized that the fluid identification device 122 is merely exemplary in nature, and various additional configurations may be used that have not necessarily been depicted in FIGS. 1-7 in the interest of clarity. Moreover, non-limiting additional components may be present, including, but not limited to, valves, condensers, adapters, joints, gauges, sensors, compressors, pressure controllers, pressure sensors, flow rate controllers, flow rate sensors, temperature sensors, and the like. As such, it should be clearly understood that the examples illustrated by FIGS. 1-7 are merely a general application of the principles of this disclosure in practice, and a wide variety of other examples are possible. Therefore, the scope of this disclosure is not limited in any manner to the details of FIGS. 1-7 as described herein.

It is to be recognized that the fluid identification device may also directly or indirectly affect the various downhole equipment and tools that may contact the fluid identification device disclosed herein. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., fluid control devices, autonomous fluid control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the apparatus, methods, and systems generally described above and depicted in FIGS. 1-7.

Provided are methods for measuring the oil to water ratio of a wellbore fluid. An example method comprises flowing the wellbore fluid into a flow path of a fluid identification device disposed on the outside of a wellbore tubing and within a wellbore annulus. The fluid identification device comprises a shroud, the flow path disposed within the shroud that opens to the wellbore annulus and fluidically links the wellbore annulus to the wellbore tubing thereby allowing fluid flow through the flow path from the wellbore annulus to the wellbore tubing, and an alternating current electrical sensor disposed within the flow path. The method further comprises measuring a property of the wellbore fluid with the alternating current electrical sensor when the wellbore fluid has flowed into the flow path and determining the oil to water ratio of the wellbore fluid that flowed through the flow path.

Additionally or alternatively, the method may include one or more of the following features individually or in combination. The alternating current electrical sensor may comprise a capacitive sensor. The alternating current electrical sensor may comprise an inductive sensor. The alternating current electrical sensor may comprise a capacitive sensor and an inductive sensor. The fluid property may comprise a dielectric permittivity, a magnetic permeability, a resistivity, or a combination thereof. The alternating current electrical sensor may be encapsulated. The alternating current electrical sensor may comprise a transmitting portion and a receiving portion. The transmitting portion and receiving portion may be arranged in a series with one another, orthogonal to one another, or in a spiral with one another. The transmitting portion and the receiving portion may be arranged perpendicular to the direction of the fluid flow or arranged parallel to the direction of fluid flow. The method may further comprise obtaining voltage measurements for the wellbore fluid at different frequencies as the wellbore fluid is in the flow path. The method may further comprise comparing the voltage measurements to graphs of the resistivity vs. the voltage, the permittivity vs. the voltage, or a combination thereof.

Provided is a fluid identification device. An example fluid identification device comprises a shroud, a flow path within the shroud that opens to a wellbore annulus and fluidically links the wellbore annulus to a wellbore tubing thereby allowing a wellbore fluid to flow through the flow path from the wellbore annulus to the wellbore tubing, and an alternating current electrical sensor disposed within the flow path configured to measure a property of the wellbore fluid to determine the oil to water ratio of the fluid as it flows through the flow path; wherein the fluid identification device is disposed on the outside of the wellbore tubing and within the wellbore annulus.

Additionally or alternatively, the fluid identification device may include one or more of the following features individually or in combination. The alternating current electrical sensor may comprise a capacitive sensor. The alternating current electrical sensor may comprise an inductive sensor. The alternating current electrical sensor may comprise a capacitive sensor and an inductive sensor. The fluid property may comprise a dielectric permittivity, a magnetic permeability, a resistivity, or a combination thereof. The alternating current electrical sensor may be encapsulated. The alternating current electrical sensor may comprise a transmitting portion and a receiving portion. The transmitting portion and receiving portion may be arranged in a series with one another, orthogonal to one another, or in a spiral with one another. The transmitting portion and the receiving portion may be arranged perpendicular to the direction of the fluid flow or arranged parallel to the direction of fluid flow.

Provided are systems for measuring the oil to water ratio of a wellbore fluid. An example system comprises a fluid identification device comprising a shroud, a flow path within the shroud that opens to a wellbore annulus and fluidically links the wellbore annulus to a wellbore tubing thereby allowing the wellbore fluid to flow through the flow path from the wellbore annulus to the wellbore tubing, and an alternating current electrical sensor disposed within the flow path configured to measure a property of the wellbore fluid to determine the oil to water ratio of the fluid as it flows through the flow path; wherein the fluid identification device is disposed on the outside of the wellbore tubing and within the wellbore annulus. The system further comprises the wellbore tubing and the fluid identification device is coupled to the exterior of the wellbore tubing.

Additionally or alternatively, the system may include one or more of the following features individually or in combination. The alternating current electrical sensor may comprise a capacitive sensor. The alternating current electrical sensor may comprise an inductive sensor. The alternating current electrical sensor may comprise a capacitive sensor and an inductive sensor. The fluid property may comprise a dielectric permittivity, a magnetic permeability, a resistivity, or a combination thereof. The alternating current electrical sensor may be encapsulated. The alternating current electrical sensor may comprise a transmitting portion and a receiving portion. The transmitting portion and receiving portion may be arranged in a series with one another, orthogonal to one another, or in a spiral with one another. The transmitting portion and the receiving portion may be arranged perpendicular to the direction of the fluid flow or arranged parallel to the direction of fluid flow. The fluid identification device may further comprise a screen. The screen may comprise a sand screen, a gravel filter, a mesh, or slotted tubing.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps. The systems and methods can also "consist essentially of" or "consist of the various components and steps." Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as ranges from any lower limit may be combined with any other lower limit to recite a range not explicitly recited. In the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

One or more illustrative examples incorporating the examples disclosed herein are presented. Not all features of a physical implementation are described or shown in this application for the sake of clarity. Therefore, the disclosed systems and methods are well adapted to attain the ends and advantages mentioned, as well as those that are inherent therein. The particular examples disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown other than as described in the claims below. It is therefore evident that the particular illustrative examples disclosed above may be altered, combined, or modified, and all such variations are considered within the scope of the present disclosure. The systems and methods illustratively disclosed herein may suitably be practiced in the absence of any element that is not specifically disclosed herein and/or any optional element disclosed herein.

Although the present disclosure and its advantages have been described in detail, it should be understood that various changes, substitutions and alterations can be made herein without departing from the spirit and scope of the disclosure as defined by the following claims.

What is claimed is:

1. A fluid identification device comprising:
a shroud, a flow path within the shroud that opens to a wellbore annulus and fluidically links the wellbore annulus to a wellbore tubing thereby allowing a wellbore fluid to flow through the flow path from the wellbore annulus to the wellbore tubing, an alternating current electrical sensor disposed within the flow path configured to measure a property of the wellbore fluid to determine the oil to water ratio of the fluid as it flows through the flow path; wherein the fluid identification device is disposed on the outside of the wellbore tubing and within the wellbore annulus, wherein the alternating current electrical sensor comprises a receiving portion and a transmitting portion; wherein the receiving portion and the transmitting portion comprise capacitive sensor portions that are circumferential around the flow path; and wherein the capacitive sensor portions are separated from the wellbore fluid with a polymer; and a flow conditioner disposed within the flow path.

2. The fluid identification device of claim 1, wherein the alternating current electrical sensor additionally comprises an inductive sensor.

3. The fluid identification device of claim 1, wherein the fluid property comprises a dielectric permittivity, a magnetic permeability, a resistivity, or a combination thereof.

4. The fluid identification device of claim 1, wherein the transmitting portion and receiving portion are arranged in a series with one another, orthogonal to one another, or in a spiral with one another.

5. The fluid identification device of claim 1, wherein the transmitting portion and the receiving portion are arranged perpendicular to the direction of the fluid flow or arranged parallel to the direction of fluid flow.

6. The fluid identification device of claim 1, wherein the flow conditioner is a static mixer.

7. The fluid identification device of claim 1, wherein the flow conditioner is upstream of the alternating current electrical sensor.

8. The fluid identification device of claim 1, wherein the flow conditioner increases turbulence of the wellbore fluid.

9. A method for measuring the oil to water ratio of a wellbore fluid, the method comprising:

flowing the wellbore fluid into a flow path of a fluid identification device disposed on the outside of a wellbore tubing and within a wellbore annulus, the fluid identification device comprising:
 a shroud,
 the flow path disposed within the shroud that opens to the wellbore annulus and fluidically links the wellbore annulus to the wellbore tubing thereby allowing fluid flow through the flow path from the wellbore annulus to the wellbore tubing,
 an alternating current electrical sensor disposed within the flow path, wherein the alternating current electrical sensor comprises a receiving portion and a transmitting portion; wherein the receiving portion and the transmitting portion comprise capacitive sensor portions that are circumferential around the flow path; and wherein the capacitive sensor portions are separated from the wellbore fluid with a polymer; and
 a flow conditioner disposed within the flow path; and
measuring a property of the wellbore fluid with the alternating current electrical sensor when the wellbore fluid has flowed into the flow path; and determining the oil to water ratio of the wellbore fluid that flowed through the flow path.

10. The method of claim 9, wherein the alternating current electrical sensor additionally comprises an inductive sensor.

11. The method of claim 9, wherein the fluid property comprises a dielectric permittivity, a magnetic permeability, a resistivity, or a combination thereof.

12. The method of claim 10, further comprising obtaining voltage measurements for the wellbore fluid at different frequencies as the wellbore fluid is in the flow path.

13. The method of claim 12, further comprising comparing the voltage measurements to graphs of resistivity vs. voltage, permittivity vs. voltage, or a combination thereof.

14. The method of claim 9, wherein the flow conditioner is a static mixer.

15. The method of claim 9, wherein the flow conditioner is upstream of the alternating current electrical sensor.

16. The method of claim 9, wherein the flow conditioner increases turbulence of the wellbore fluid.

17. The method of claim 9, wherein the transmitting portion and receiving portion are arranged in a series with one another, orthogonal to one another, or in a spiral with one another.

18. The method of claim 9, wherein the transmitting portion and the receiving portion are arranged perpendicular to the direction of the fluid flow or arranged parallel to the direction of fluid flow.

19. A system for measuring the oil to water ratio of a wellbore fluid, the system comprising:

a fluid identification device comprising:
 a shroud,
 a flow path within the shroud that opens to a wellbore annulus and fluidically links the wellbore annulus to a wellbore tubing thereby allowing the wellbore fluid to flow through the flow path from the wellbore annulus to the wellbore tubing,
 an alternating current electrical sensor disposed within the flow path configured to measure a property of the wellbore fluid to determine the oil to water ratio of the fluid as it flows through the flow path; wherein the fluid identification device is disposed on the outside of the wellbore tubing and within the wellbore annulus, wherein the alternating current electrical sensor comprises a receiving portion and a transmitting portion; wherein the receiving portion and the transmitting portion comprise capacitive sensor portions that are circumferential around the flow path; and wherein the capacitive sensor portions are separated from the wellbore fluid with a polymer; and
 a flow conditioner disposed within the flow path; and
the wellbore tubing; wherein the fluid identification device is coupled to the exterior of the wellbore tubing.

20. The system of claim 19, wherein the alternating current electrical sensor additionally comprises an inductive sensor.

21. The system of claim 19, wherein the fluid property comprises a dielectric permittivity, a magnetic permeability, a resistivity, or a combination thereof.

22. The system of claim 19, wherein the flow conditioner is a static mixer.

23. The system of claim 19, wherein the flow conditioner is upstream of the alternating current electrical sensor.

24. The system of claim 19, wherein the flow conditioner increases turbulence of the wellbore fluid.

25. The system of claim 19, wherein the transmitting portion and receiving portion are arranged in a series with one another, orthogonal to one another, or in a spiral with one another.

26. The system of claim 19, wherein the transmitting portion and the receiving portion are arranged perpendicular to the direction of the fluid flow or arranged parallel to the direction of fluid flow.

* * * * *

UNITED STATES PATENT AND TRADEMARK OFFICE
CERTIFICATE OF CORRECTION

PATENT NO. : 12,152,487 B2
APPLICATION NO. : 17/836962
DATED : November 26, 2024
INVENTOR(S) : Michael Linley Fripp et al.

Page 1 of 1

It is certified that error appears in the above-identified patent and that said Letters Patent is hereby corrected as shown below:

In the Claims

At Column 14, Line 6, delete "10" and insert therefor --9--.

Signed and Sealed this
Thirty-first Day of December, 2024

Derrick Brent
*Acting Director of the United States Patent and Trademark Office*